(12) United States Patent
Shiibashi (10) Patent No.: US 8,357,097 B2
(45) Date of Patent: Jan. 22, 2013

(54) SMALL-SCALE DIAGNOSTIC SYSTEM AND DISPLAY CONTROL METHOD

(75) Inventor: Takao Shiibashi, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 608 days.

(21) Appl. No.: 12/527,118

(22) PCT Filed: Feb. 8, 2008

(86) PCT No.: PCT/JP2008/052119
§ 371 (c)(1),
(2), (4) Date: Aug. 13, 2009

(87) PCT Pub. No.: WO2008/099777
PCT Pub. Date: Aug. 21, 2008

(65) Prior Publication Data
US 2010/0042003 A1    Feb. 18, 2010

(30) Foreign Application Priority Data
Feb. 16, 2007    (JP) ................................. 2007-036276

(51) Int. Cl.
*A61B 8/14*    (2006.01)
(52) U.S. Cl. ...................................... 600/459
(58) Field of Classification Search ................... 600/459
See application file for complete search history.

(56) References Cited

U.S. PATENT DOCUMENTS

| 5,334,851 A | 8/1994 | Good et al. | |
|---|---|---|---|
| 2002/0080918 A1* | 6/2002 | Sako ............................ | 378/115 |

FOREIGN PATENT DOCUMENTS

| EP | 1811425 A1 | 7/2007 |
|---|---|---|
| JP | 9-117417 A | 5/1997 |
| JP | 2000-271120 A | 10/2000 |
| JP | 2002-159476 A | 6/2002 |
| JP | 2002-311524 A | 10/2002 |
| JP | 2004-21380 A | 1/2004 |
| JP | 2006-48301 A | 2/2006 |
| JP | 2006-133907 A | 5/2006 |
| JP | 2006-133908 A | 5/2006 |

(Continued)

OTHER PUBLICATIONS

International Search Report for International Application No. PCT/JP2008/052119 dated Mar. 4, 2008 with English translation.
Notice of Reasons for Refusal for Japanese Patent Application No. 2008-558071, drafted Nov. 9, 2011, with English translation.

*Primary Examiner* — Brian Casler
*Assistant Examiner* — Saurel J Selkin
(74) *Attorney, Agent, or Firm* — Cantor Colburn LLP (57) ABSTRACT

A small-scale diagnostic system and a display control method are provided. In the diagnostic system, while image data on a patient is displayed on a screen of a medical image control device, when image data on another patient is received from an image generating device, and the medical doctor wants to display the received image data on the another patient on the screen for examining the image and diagnosing the another patient, the displayed image on the screen can be switched to that of the image data on the another patient by a simple operation of depressing a patient selection button. This enables the medical doctor to perform image diagnosis efficiently in a small-scale facility such as a clinic.

2 Claims, 7 Drawing Sheets

FOREIGN PATENT DOCUMENTS

| | | |
|---|---|---|
| JP | 2006-133909 A | 5/2006 |
| JP | 2006-133910 A | 5/2006 |
| WO | 2006/049077 A1 | 5/2006 |
| WO | 2007/099735 A1 | 9/2007 |
| WO | 2007/116719 A1 | 10/2007 |
| WO | 2007/141985 A1 | 12/2007 |

* cited by examiner

| RADIOGRAPHING ID | PATIENT ID | NAME | BODY PART | | | CASSETTE ID | ... |
|---|---|---|---|---|---|---|---|
| 10240001 | 200510240001 | ICHIRO SATO | CHEST | AP | FRONT | | ... |
| 10240002 | | | CHEST | | FRONT | | ... |
| 10240003 | | | CHEST | | FRONT | | ... |
| 10240004 | 200510240002 | ICHIRO SUZUKI | ABDOMEN | | | | ... |
| 10240005 | 200510240003 | HANAKO YAMADA | BREAST | L | MLO | | ... |
| 10240006 | | | BREAST | R | MLO | | ... |
| 10240007 | | | BREAST | L | CC | | ... |
| 10240008 | | | BREAST | R | CC | | ... |

FIG. 8b

| RADIOGRAPHING ID | PATIENT ID | NAME | BODY PART | | | CASSETTE ID | ... |
|---|---|---|---|---|---|---|---|
| 10240001 | 200510240001 | ICHIRO SATO | CHEST | AP | FRONT | 000100 | ... |
| 10240002 | | | CHEST | | FRONT | 000101 | ... |
| 10240003 | | | CHEST | | FRONT | 000102 | ... |
| 10240004 | 200510240002 | ICHIRO SUZUKI | ABDOMEN | | | | ... |
| 10240005 | 200510240003 | HANAKO YAMADA | BREAST | L | MLO | | ... |
| 10240006 | | | BREAST | R | MLO | | ... |
| 10240007 | | | BREAST | L | CC | | ... |
| 10240008 | | | BREAST | R | CC | | ... |

SMALL-SCALE DIAGNOSTIC SYSTEM AND DISPLAY CONTROL METHOD

CROSS REFERENCE TO RELATED APPLICATIONS

This is a U.S. national stage of application No. PCT/JP2008/052119, filed on 8 Feb. 2008. Priority under 35 U.S.C. §119(a) and 35 U.S.C. §365(b) is claimed from Japanese Application No. 2007-036276, filed 16 Feb. 2007, the disclosure of which is also incorporated herein by reference.

TECHNICAL FIELD OF THE INVENTION

The present invention relates to small-scale diagnostic systems that are used mainly in small-scale medical facilities, and to display control methods in medical image management apparatuses used in small-scale diagnostic systems.

BACKGROUND TECHNOLOGY

Conventionally, diagnostic systems have been known in which a patient visiting a hospital is radiographed by a technician as the target of inspection using an image generating apparatus such as a CR (Computed Radiography) apparatus, or an FPD (Flat Panel Detector) apparatus or the like, and the obtained images are subjected to image processing such as gradation processing so as to make it presentable for diagnosis, and then the image whose image processing has been completed is output and is provided to the doctor for image interpretation.

In such a diagnostic system, the diagnosis is carried out with a plurality of people in charge sharing the different roles such as, a person in charge (receptionist) for receiving the patient who has visited the hospital and issuing an order for radiography, a person in charge (technician) who actually radiographs the patient in the radiographing room and generates the image data, a person in charge (a technician who is designated from ordinary technicians) who judges whether or not it is possible to submit the obtained image for diagnosis which has been subjected to processing such as gradation characteristics, etc., and if necessary carries out correction of the contrast or the density, and a person in charge of interpreting the image (doctor) who judges the presence or absence of disease (diagnoses) based on the images.

Further, in large-scale medical facilities (hereinafter referred to as large-scale facilities) in which conventional diagnostic systems were assumed to be used, there was a plurality of image generating apparatuses and a plurality of technicians operating them, and even the consoles operating the image generating apparatuses, or the viewers. through which the doctors check the image data are also provided individually with their respective roles having been determined. Because of this, there is the possibility of mistakes being made between the patients and the image data. In view of this and in order to prevent this, a system has been proposed (see, for example, Patent Document 1) in which all the apparatuses are coordinated with each other through a network, IDs are issued in each apparatus, and correspondences are established between results of the work processes carried out in each apparatus.

In such a system, the places of taking charge of the above roles are frequently at distant locations within a large hospital, such as the reception being in the first floor, radiology department being in the basement floor, and also, inside the radiology department, it is a common thing that a plurality of patients are radiographed by a plurality of technicians using a plurality of radiographing apparatuses at the same time, and plurality of patients are waiting all the time at each process, and IDs are issued for each work at each process so that there is no mistake in establishing correspondences between the images generated and the individual patients and the establishment of correspondences is done via a network of an HIS (Hospital Information System) or an RIS (Radiology Information System) (see, for example, Patent Document 2 and Patent Document 3).

Figure 8A:
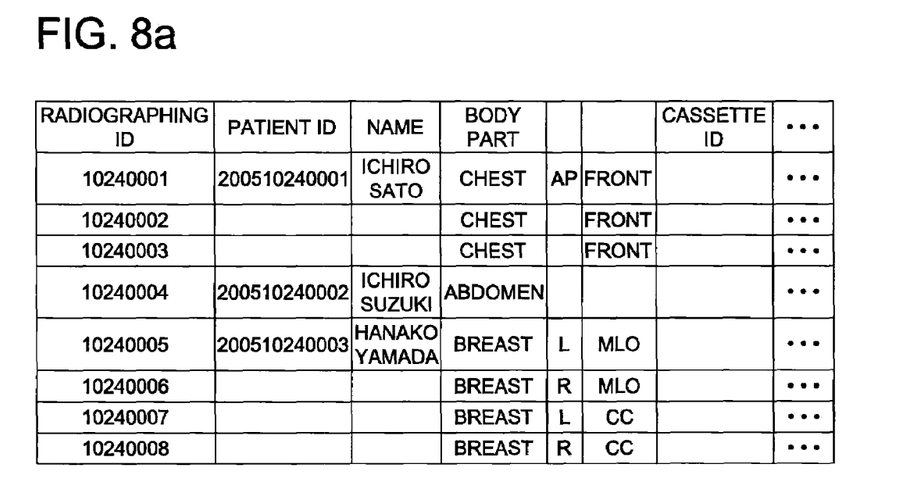
FIG. 8a is diagram showing an example of a list registered at the reception counter in a conventional diagnostic system.

For example, at the reception counter in first floor, the contents of radiography are determined based on the main complaints made by the patient which are then registered along with the patient name. Because of this, a patient list such as the one shown in FIG. 8a gets prepared. Additions are made constantly to said patient list, and it is displayed in the work station (hereinafter referred to as "WS") for the receptionist in first floor. At the same time, said patient list is displayed, via the network of RIS or HIS, in the console in the radiology department in the basement floor (here, a "console" is a work station that is placed in the radiology department and that displays the settings of the radiography conditions, or the radiography order data information of RIS or HIS, or the images obtained by radiographing a patient). Further, number of console units is very often made plural in order to increase the distributed processing efficiency, and these are connected mutually via the network, and when a particular radiography ID is selected in any console, in order to prevent duplicate radiography among multiple technicians, a method is used of announcing the fact that processing is being made in that patient list (this can be a flashing display, or changing the color of display, or giving a warning beep sound when the same inspection is specified).

Figure 8B:
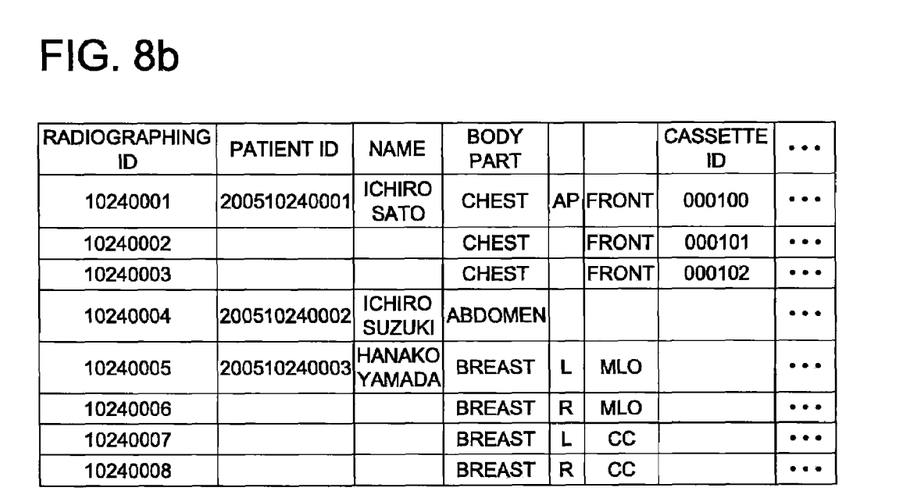
FIG. 8b is a diagram showing an example in which the technician of the radiology department has registered a cassette in the list shown in FIG. 5a in a conventional diagnostic system.

The technician in the radiology department, using a nearby console, selects the radiography ID to be carried out from now on from the patient list being displayed, and registers the ID (cassette ID) of the X-ray image conversion medium (a cassette) to be used. Because of this, as is shown in FIG. 8b, the registered cassette ID is displayed in the cassette ID column of the patient list. For example, the technician moves to the radiographing room carrying three cassettes, and carries out radiography of the patient. After that, the used cassettes are read out by the reading apparatus. The reading apparatus reads out the cassette ID affixed to the inserted cassette transmits the image data after adding that cassette ID to it, and finally correspondence is established between the radiography ID (patient ID) and the generated image data. The generated image data is transmitted to the console in which the technician selected said radiography ID and is displayed in that console. At this stage, radiography positioning is confirmed, and radiography is done again if there is any defect in positioning, and a judgment is made as to whether or not correction of density or contrast, or frequency enhancement processing is to be made. After that, that image is stored in the image interpretation awaiting (diagnosis awaiting) server. An image interpreting doctor selects and displays in a workstation in the image interpretation room (very often this is a high resolution monitor for the functions of a viewer) the images of a particular patient from among the images stored in said image interpretation awaiting server, and carries out image interpretation (diagnosis).

In a large-scale facility in which a diagnostic system described above is used, the image interpreting doctor carries out interpretation of images as a specialist, and in preparation for the day when an image interpreting doctor carries out image interpretation, the radiography of all the parts of the patients to be radiographed is completed beforehand, and the information necessary for diagnosis is collected. Therefore, it is very common that an image interpreting doctor who has completed the image interpretation and diagnosis for one patient goes on to carry out the image interpretation and diagnosis for another patient. In other words, an image interpreting doctor, at the workstation in the image interpreting room, selects and displays the image of a patient who is the target from among the images stored in the image interpretation awaiting server, carries out image interpretation and diagnosis, and after completion of the image interpretation and diagnosis of one patient, selects and displays the image of the next patient from the images stored in the image interpretation awaiting server, and carries out the image interpretation and diagnosis of the next patient.

Patent Document 1: Specification of U.S. Pat. No. 5,334,851.
Patent Document 2: Unexamined Japanese Patent Application Publication No. 2002-159476.
Patent Document 3: Unexamined Japanese Patent Application Publication No. 2002-311524.

DISCLOSURE OF THE INVENTION

Problems to be Solved by the Invention

On the one hand, according to the investigations made by the present inventors and others, in the case of relatively small scale medical facilities (hereinafter referred to as small-scale facilities) such as a medical practitioner's office or a clinic, the work flow is different from that in a large-scale facility, and in most cases, there is only one doctor who carries out diagnosis of patients, and even the number of image generating apparatuses installed is small. The doctor often controls the X-ray emission switch after the assistant has carried out the positioning of the patient and hearing from the assistant that the positioning of the patient is complete, or all the operations including the positioning of the patient are done by the doctor himself or herself.

Further, in a small-scale facility, there are many cases where image diagnosis is not carried out after waiting for the collection of all images of one patient (for example, images captured by a CR apparatus and images captured by an ultrasonic diagnostic apparatus) as in a large-scale facility, but the diagnosis is started at any time from the image that is received in the viewer (display apparatus) in the consultation room. For example, now there is a patient 'a' needing radiography using a CR apparatus and photography using an ultrasonic diagnostic apparatus, and there is a patient 'b' needing radiography using a CR apparatus of the same body part as patient 'a'. Considering a reason such as convenience of setting the apparatus or patient 'b' being an emergency patient, after carrying out radiography of patient 'a' and patient 'b' using CR apparatus, the patient 'a' is photographed in the ultrasonic diagnostic apparatus. In such cases, the images are received in the viewer in the consultation room in the sequence of CR image of patient 'a'→CR image of patient 'b'→ultrasonic photography image of patient 'a'. There are cases in which the doctor waits until all the images of patient 'a' are received and carries out examination and diagnosis from an image of patient 'a' after displaying the set of images of patient 'a', and carries out examination and diagnosis of patient 'b' after completing the examination (including diagnosis from an image) of patient 'a', for example. However, if the patient 'b' is an emergency patient, it may be necessary to display the image of patient 'b' and carry out diagnosis of patient 'b' in the middle of diagnosis from an image of patient 'a'.

However, in the conventional diagnostic systems of large-scale facilities, since the above work flow in small-scale facilities has not been considered, even if such a system is applied for a small-scale facility it cannot be said to be optimum.

An object of the present invention is to make it possible for doctors to carry out image diagnosis efficiently in a small-scale medical facility such as a medical practitioner's office or the like.

Means for Solving the Problems

The above object can be achieved by structures such as the following.

1. A small-scale diagnostic system in which image generating apparatuses that photograph patient body parts that are targets of diagnosis and generate and transmit image data, and a medical image management apparatus that receives the image data generated in said image generating apparatuses and stores in a storage section said received image data and patient information of said patients while establishing correspondence between them are connected, wherein said medical image management apparatus is provided with a display section that displays in a display screen the image data stored in said storage section with correspondence established with patient information patient by patient, and a display control section that displays in said display section a patient selection button for inputting an instruction for changing to the screen display of image data of another patient during the screen display of image data of one patient, and changes the screen display of image data in said display section to the screen display of another patient in accordance with the instruction input operation of said displayed patient selection button.

2. A small-scale diagnostic system according to structure 1, wherein in said patient selection button, the patient information of another patient is displayed who is the destination of selection of screen display to be conducted by said patient selection button.

3. A small-scale diagnostic system according to structure 2, wherein every time correspondence of patient information other than the patient information being displayed already in the patient selection button is established with the image data received from said image generating apparatus, said display control section generates a patient selection button displaying said patient information whose correspondence has been established and displays it in said display section.

4. A small-scale diagnostic system according to any one of structures 1 through 3, which is provided with a patient information input section of inputting patient information of a patient who is the target of examination, and if three or more of said patient selection buttons are being displayed, although said display control section accepts selection instruction of changing from the screen display of said patient who is the target of examination to the screen display of another patient using said patient selection button, it does not accept instruction for changing the screen display between patients other than said patient who is the target of examination, and does not change the screen display between patients other than said patient who is the target of examination.

5. A small-scale diagnostic system according to structure 4, wherein during the screen display of a patient other than said patient who is the target of examination, said display control section carries out blinking display of the patient selection button displaying the patient information of said patient who is the target of examination.

6. A display control method of image data in a medical image management apparatus that receives the image data generated in image generating apparatuses that photograph patient body parts that are targets of diagnosis and generate and transmit the image data, and stores in a storage section said received image data and patient information of said patients while establishing correspondence between them, wherein said display control method has a step of displaying in a display screen the image data stored in said storage section with correspondence established with patient information patient by patient, a step of displaying in said display section a patient selection button for inputting an instruction for changing to the screen display of image data of another patient during the screen display of image data of one patient, and a step of changing the screen display of image data in said display section to the screen display of another patient in accordance with the instruction input operation of said displayed patient selection button.

7. A display control method according to structure 6 wherein in said patient selection button, the patient information of another patient is displayed who is the destination of selection of screen display to be conducted by said patient selection button.

8. A display control method according to structure 7 which has steps of generating a patient selection button displaying said patient information whose correspondence has been established and displaying it in said display section, every time correspondence of patient information other than the patient information being displayed already in the patient selection button is established with the image data received from said image generating apparatus.

9. A display control method according to any one of structures 6 though 8 which has a step of inputting patient information of a patient who is the target of examination, and, if three or more of said patient selection buttons are being displayed, although selection instruction is accepted of changing from the screen display of said patient who is the target of examination to the screen display of another patient using said patient selection button, an instruction is not accepted for changing the screen display between patients other than said patient who is the target of examination, and no change of the screen display is made between patients other than said patient who is the target of examination.

10. A display control method according to structure 9 above which has a step of carrying out blinking display of the patient selection button displaying the patient information of said patient who is the target of examination, during the screen display of a patient other than said patient who is the target of examination.

EFFECT OF THE INVENTION

According to the present invention, when the image data of a different patient is received from an image generating apparatus while a doctor is making screen display of the image data of one patient in a medical image management apparatus, if the doctor wishes to display in the screen the received image data of the other patient and to carry out examination and diagnosis, it is possible to change the screen display to the image data of the other patient by making a simple operation of pressing the patient selection button, and in a small-scale facility such as a medical practitioner's office, it is possible to provide a small-scale diagnostic system and display control method with which a doctor can carry out image diagnosis efficiently.

DESCRIPTION OF SYMBOLS

1 Small-scale diagnostic system
2 Image generating apparatus
2a Ultrasonic diagnosis apparatus
2b Endoscopic apparatus
2c CR apparatus
3 Control apparatus
4 Testing apparatus
5 Reception apparatus
6 Network
31 CPU
32 RAM
321 Received data storage section
33 Storage section
34 Input section
35 Display section
351 Medical care summary screen
352 Correspondence establishment instruction screen
36 Communication section
37 I/F
38 Image database
39 Test information database
40 Bus

DETAILED DESCRIPTION OF THE PREFERRED EMBODIMENTS

In the following, a preferred embodiment of a small-scale diagnostic system according to the present invention is described referring to FIG. 1 to FIG. 7. However, the present invention shall not be limited to the examples shown in the figures.

Figure 1:
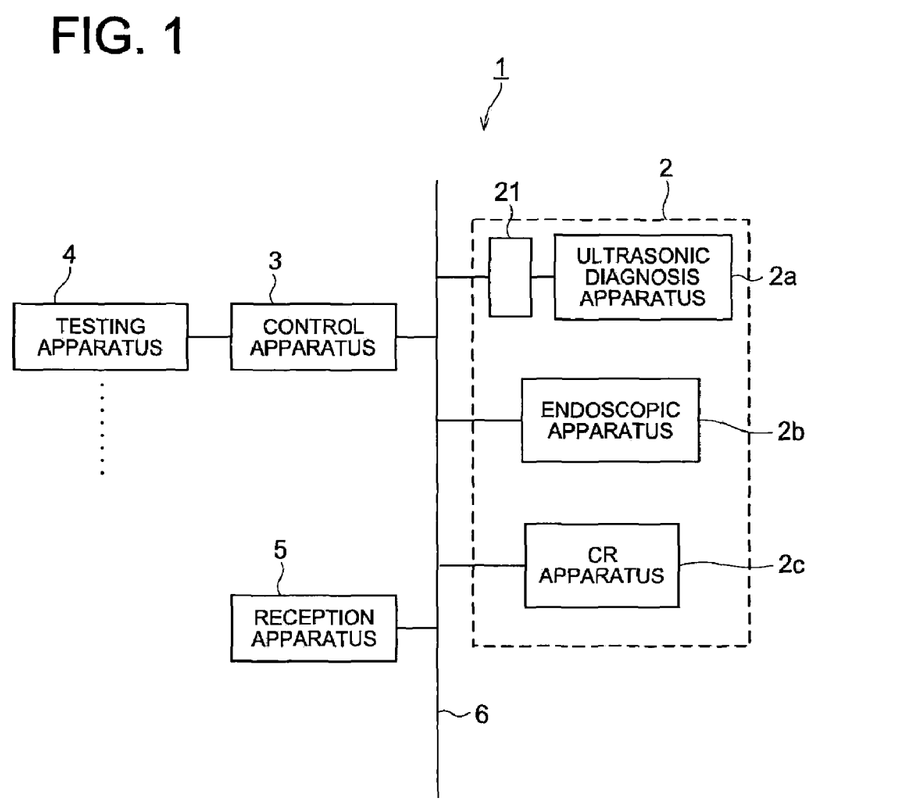
FIG. 1 is a diagram showing an example of the overall configuration of a small-scale diagnostic system according to the present invention.
Figure 2:
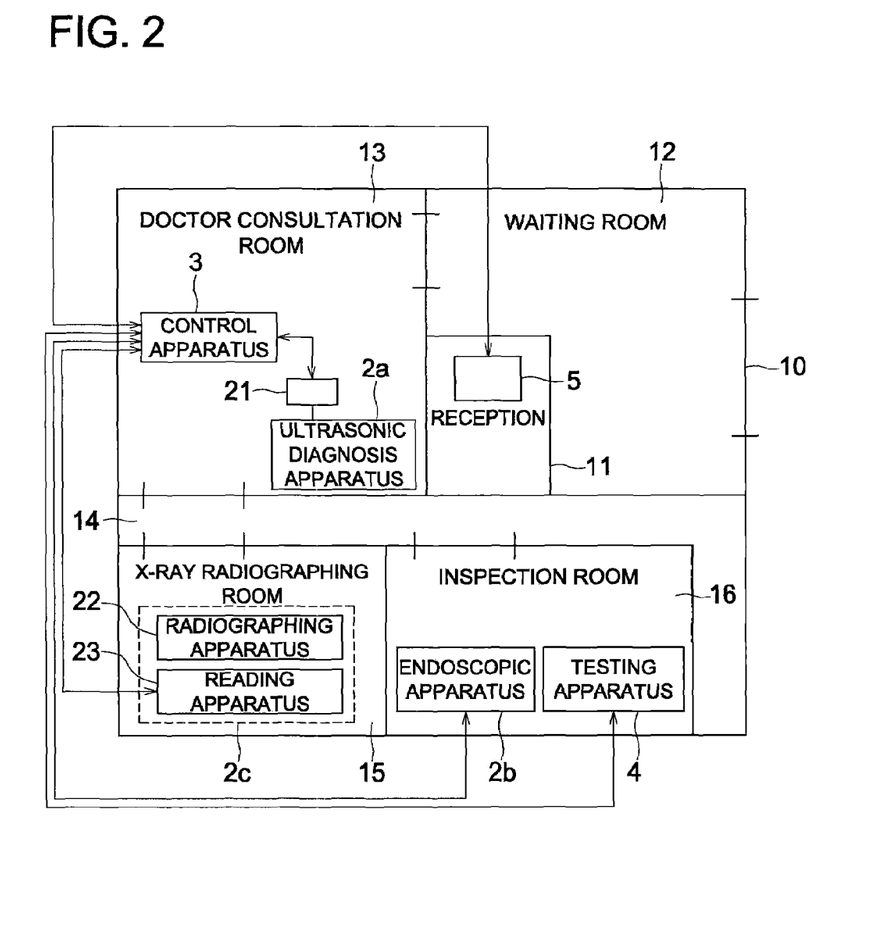
FIG. 2 is a diagram showing an example of placement of different apparatuses in a medical facility when a small-scale diagnostic system shown in FIG. 1 is used.

To begin with, the configuration is described here. FIG. 1 is a diagram showing an example of the system configuration of a small-scale diagnostic system 1 according to the present invention, and FIG. 2 is a diagram showing an example of placement of different apparatuses in a medical facility when the small-scale diagnostic system 1 is used.

The small-scale diagnostic system 1 is a system that is used in a relatively small-scale medical facility such as a medical practitioner's office or a clinic, and unlike a system such as in a large-scale diagnostic system, in which the order information (test order information, radiography order information) for a patient is generated in advance, and is issued, and radiography is carried out, and the correspondence between the obtained image data and the order information are established, this is a system in which the photographing of the patient is done first, and after the image data of captured image is generated, the doctor establishes correspondence between the patient information and the image data.

The small-scale diagnostic system 1 is a system that is used in a relatively small-scale medical facility such as a medical practitioner's office or a clinic, and is configured as shown in FIG. 1 to have an ultrasonic diagnosis apparatus 2a, an endoscopic apparatus 2b, a CR apparatus 2c which are image generating apparatuses 2, a control apparatus 3, a testing apparatus 4, and a reception apparatus 5, and the image generating apparatuses 2, the control apparatus 3, and the reception apparatus 5 are, for example, connected to a communication network 6 (hereinafter referred to merely as a network) such as a LAN (Local Area Network), via a switching hub or the like, that is not shown in the figure. It is desirable that the control apparatus 3 is a workstation (WS) that is installed in the consultation room where a doctor is present at all times. Further, the WS that operates as this control apparatus 3 can also be configured so that it controls the starting or processing conditions of the different image generating apparatuses 2.

As a medical relation communication method, generally, the DICOM (Digital Image and Communications in Medicine) standard is used, and the DICOM MWM (Modality Worklist Management) or the DICOM MPPS (Modality Performed Procedure Step) is used in the communication between the different apparatuses connected to a LAN.

For example, in a small-scale diagnostic system such as a medical practitioner's office or a clinic, the different apparatuses are places as shown in FIG. 2. To be more specific, upon entering the entrance 10, there is the waiting room 12 and the reception counter 11 where the patient is received. A person in charge of the counter is positioned at the reception counter 11, and this person in charge, for example, gives to each arriving patient a reception number tag in which a reception number has been printed to identify different patients in the order in which they are received. Further, a reception apparatus 5 is placed in the reception counter 11, and the person in charge of the counter asks the patient for the name of the patient, and others, and enters them in the reception apparatus 5 while establishing correspondence between the patient information such as the patient name and the reception number.

Next to the waiting room 12 and separated by a door, a consultation room 13 is provided, where the doctor carries out examination and diagnosis of the patient. For example, on top of a desk for consultation (not shown in the figure) inside the consultation room 13, a control apparatus 3 is placed for displaying, for the diagnosis by the doctor, the captured images obtained by photographing the diagnosis target body parts of the patient, and the test results related to the tests carried out for the patient, or the like. Further, in the consultation room 13, an ultrasonic diagnosis apparatus 2a is provided, which has low necessity for carrying out diagnosis in a partitioned space from the point of view of privacy of the patient.

Further, opposite the consultation room 13 and separated by a corridor 14, an X-ray radiography room 15 is provided for carrying out radiography. In the radiography room 15, a CR apparatus 2c is installed, which is configured to have a radiographing apparatus 22 and a reading apparatus 23. In addition, next to the radiography room 15, an inspection room 16 is provided, and inside the inspection room 16, an endoscopic apparatus 2b and a testing apparatus 4 are installed.

In the following, the configurations of the different apparatuses of the small-scale diagnostic system 1 are described.

The image generating apparatuses 2, for example, the ultrasonic diagnosis apparatus 2a, the endoscopic apparatus 2b1, the CR apparatus 2c are apparatuses that photograph diagnosis target body parts of the patient as the photographed objects, carry out conversion to digital format of the photographed images, and generate the image data of the photographed images.

The ultrasonic diagnosis apparatus 2a has an ultrasonic probe that outputs ultrasonic waves, and an electronic apparatus that is connected to the ultrasonic probe and that converts the acoustic waves (echo signals) received by the ultrasonic probe into the image data of the photographed image of the tissues in the body (both of these are not shown in the figure). The ultrasonic diagnosis apparatus 2a transmits ultrasonic waves from the ultrasonic probe to the interior of the body, receives, using the ultrasonic probe again, the acoustic waves (echo signals) reflected by the tissues inside the body, and a photographic image corresponding to these echo signals is generated by the electronic apparatus.

To the ultrasonic diagnosis apparatus 2a, a conversion apparatus 21 is connected, which is a conversion device (converter) that carries out conversion from analog signals to digital signals, and the ultrasonic diagnosis apparatus 2a is connected to the network 6 via the conversion apparatus 21. By using such a conversion apparatus 21 in between, even when data is output by the ultrasonic diagnosis apparatus 2a that is in a format that is not compatible with the standards (for example, communication protocols) of other external equipment connected to the network 6, it is possible to carry out transmission and reception of data with the external equipment connected to the network 6 by carrying out appropriate conversions.

In the present preferred embodiment, the conversion apparatus 21 is provided with the function of adding, to the image data, the UID (Unique ID) for identifying the image data within the small-scale diagnostic system 1 with a format that conforms to the DICOM standards. The UID is constituted from information identifying each of the apparatuses configuring the small-scale diagnostic system 1 (hereinafter called the apparatus ID), and numbers that indicate the date and time of photography (testing). Further, in the present preferred embodiment, the apparatus ID is considered to be constituted to include information indicating the type of the image generating apparatus 2.

The endoscopic apparatus 2b is one in which a small photographing apparatus is provided at the tip part of a tube having flexibility (either of which are not shown in the figure), and the photographing apparatus is provided with an objective optical system made of, for example, optical lens, an imaging section placed at the image focusing position of the objective optical system, and an illumination section that carries out the illumination necessary for carrying out photography and that is constituted using an LED (Light Emitting Diode), or the like (all of which have not been shown in the figure). The imaging section is provided with a solid state imaging device such as, for example, a CCD (Charge Coupled Device), a CMOS (Complementary Metal-Oxide Semiconductor), which, when light enters it, carries out photoelectric conversion to an electrical signal corresponding to the amount of light entering it. The objective optical system is configured so that it focuses using an optical lens at the area that is illuminated by the illuminating section, and so that the image of that part is focused on to the solid state imaging device in the imaging section, and due to the photoelectric conversion of the light incident on the imaging device the image data of the captured image is output as an electrical signal.

The radiographing apparatus 22 which is a constituent part of the CR apparatus 2c has a radiation source not shown in the figure, emits radiation to the body part which is the target of diagnosis of the patient and captures a still image. During radiography, in the area of incidence of the radiation emitted from said radiation source, a cassette is placed having inside it a radiation image conversion plate provided with, for example, a photostimulable phosphor sheet that stores radiation energy, and an amount of radiation corresponding to the radiation transmittivity distribution of the body part that is the target of diagnosis with respect to the amount of radiation emitted from the radiation source is accumulated in the photostimulable phosphor layer of the photostimulable phosphor sheet inside the cassette, and the radiation image information of the body part that is the target of diagnosis is recorded in this photostimulable phosphor layer.

The reading apparatus 23, when a cassette in which the radiation image information of the body part that is the target of diagnosis is recorded is inserted in it, an excitation light is emitted onto the photostimulable phosphor sheet of the cassette which is inserted into the apparatus, and the photostimulated light emitted from the sheet because of this is converted photoelectrically, the image signal so obtained is A/D converted, and the image data of the captured image is generated. The CR apparatus 2c can also be an integrated type of apparatus in which the radiographing apparatus 22 and the reading apparatus 23 are integrated into one apparatus.

Further, in the reading apparatus 23 of the endoscopic apparatus 2b and of the CR apparatus 2c, there is the function of adding said UID to the generated image data, and this added UID is attached to the image data.

Figure 3:
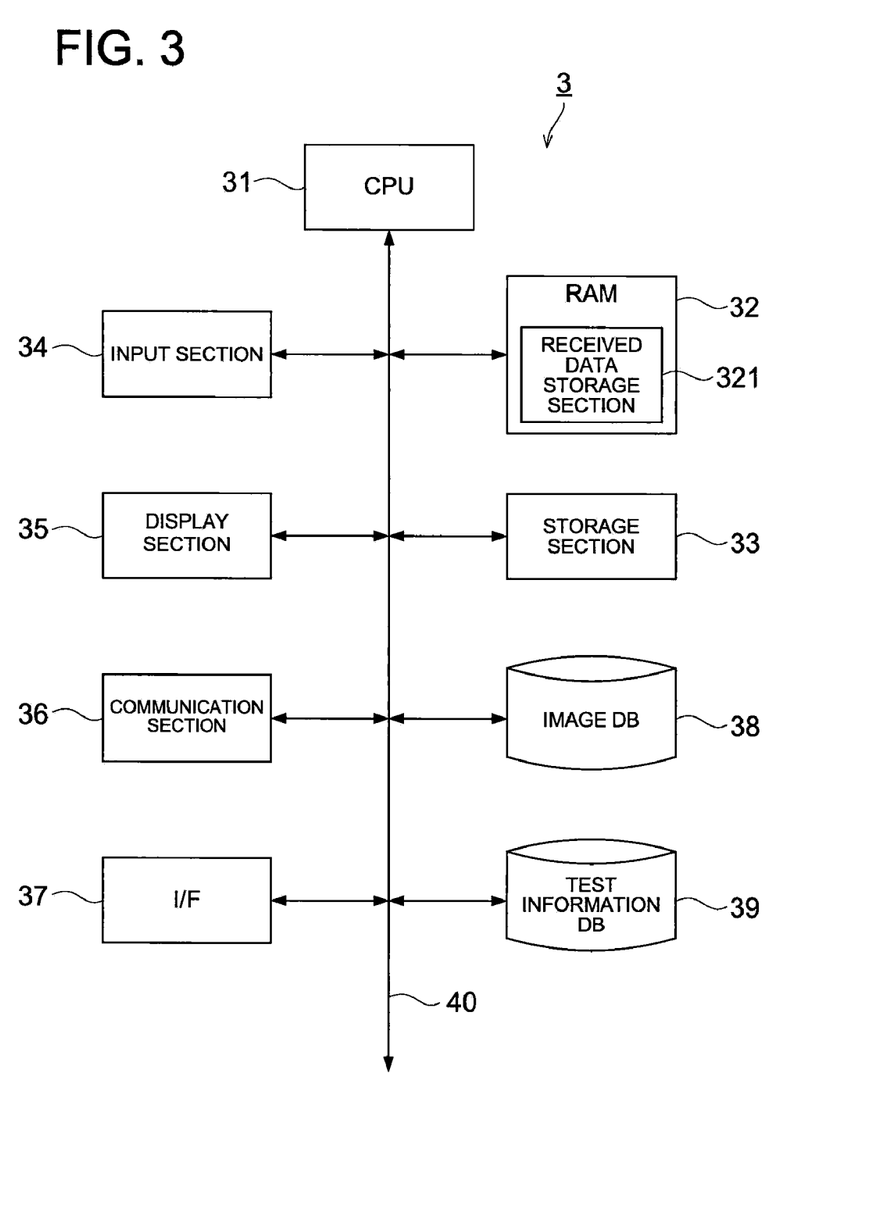
FIG. 3 is a block diagram of important parts showing the functional configuration of a control apparatus used in a small-scale diagnostic system shown in FIG. 1.

The control apparatus 3, is placed, for example, in the consultation room 13, and is a medical image management apparatus for storing the image data generated in the image generating apparatus 2 in the image data base 38 after establishing correspondence with the patient information, or for the doctor to display the image, and carry out image interpretation and diagnosis, and can also be equipped with a high resolution monitor than a monitor (display section) used in common PCs (Personal Computers). The control apparatus 3, as is shown in FIG. 3, is configured to have a CPU 31, a RAM 32, a storage section 33, an input section 34, a display section 35, a communication section 36, an I/F 37, an image data base 38, a test information data base 39, or others, and each of these sections are interconnected by a bus 40.

The CPU 31 reads out various types of programs such as system programs or processing programs stored in the storage section 33 and develops them into the RAM 32, and executes various types of processing including display control processing, which are described later, based on the programs developed into the RAM 32.

In the different types of processings that are executed and controlled by the CPU 31, the RAM 32 forms a work area for temporarily storing the various programs that are read out from the storage section 33 and that can be executed by the CPU 31, input or output data, and parameters and others. In the present preferred embodiment, the RAM 32 has a received data storage section 321 that temporarily stores the image data received from the image generating apparatuses 2 or the test data received from the testing apparatus 4.

The storage section 33 is configured to have a HDD (Hard Disk Drive), or nonvolatile memory of semiconductor or the like. In the storage section 33, not only the different types of programs as described above, but also various image processing parameters (look up table defining the gradation curve used for the gradation processing, degree of emphasis of frequency processing, etc.) in order to adjust the image data of the captured images for the image quality suitable for diagnosis are stored.

The input section 34 is configured to have a keyboard provided with cursor keys, numeric keys, and various types of function keys, and a pointing device such as a mouse, and the operation signal of depressing keys in the keyboard and the operation signals of the mouse are output to the CPU 31 as the input signals.

The display section 35, is configured to have a monitor such as a CRT (Cathode Ray Tube) monitor or an LCD (Liquid Crystal Display) monitor, and displays various types of screens according to the instructions of the display signals input from the CPU 31.

The communication section 36 is configured to have a network interface and others, and carries out transmission and reception of data with external equipment connected to the network via a switching hub.

The I/F 37, is configured to have a communication interface such as an RS-232C interface, and is an interface for connecting a testing apparatus 4 with the control apparatus 3, and controls the transmission and reception of data with the testing apparatus 4.

The image data base 38 is configured to have an HDD, and is a storage section that stores the image data of captured images while establishing correspondence with patient data. The test information data base 39 is configured to have an HDD, and is a test information storage section that stored various types of test data while establishing correspondence with patient data.

The testing apparatus 4 is configured to have a cardiac electrical wave detector apparatus that detects cardiac electrical waveform and obtains the waveform data, a vital sensor that obtains vital data such as body temperature, blood pressure, height, weight, a sound collector that obtains bioacoustic data such as pulmonary sounds, cardiac sounds, voice, and the obtained test data (the above waveform data, vital data, bioacoustic data) is transmitted to the control apparatus 3 after appending the above described UID.

The reception apparatus 5 is a computer for receiving and registering patients who have come to the clinic or medical practitioner's office, for accounting calculations, for calculating the insurance points, and others, and is configured to have a CPU, a RAM, a storage section having an HDD, an input section such as a keyboard, mouse, a display section having a CRT or an LCD display, a communication section for controlling the communication with different apparatuses connected to the network 6, (all of which are not shown in the figure). The reception apparatus 5, when an instruction is given from the input section to display the reception input screen, due to the coordinated operation of the CPU and the programs stored in the storage section, displays, in the display section, a reception input screen not shown in the figure, and when the reception information (reception number+patient information) is input from the input section via the reception input screen, prepares (updates) the patient information list of the received patient and stores it in the RAM, and transmits to the control apparatus 3 via the communication section according to a patient list transmission request from the control apparatus 3.

Next, the flow of examination of one patient is described below in a small medical facility in which a small-scale diagnostic system 1 has been used.

When a patient comes to the medical facility, at the reception counter 11, a reception number tag is assigned to the patient, and in the reception apparatus 5, an input (reception input) of the reception number of the received patient and the patient information such as the patient's name is made by operations of the input section. In the reception apparatus 5, when the reception number and the patient information of the received patient are input, a list of patient information (patient information list) is generated (or updated), and is stored in a prescribed area of the RAM. The patient information list, is generated, for example, when the first patient of the day is received and is stored in a prescribed area of the RAM, and then is updated to a new patient list every time the reception of the next patient is input.

When a patient who a reception number has been assigned to moves to the consultation room 13, an oral interview of the patient is made by the doctor, and the photography and tests that need to be carried out are determined.

When it has been decided upon oral interview that photography of the affected part is necessary, the person carrying out photography such as a photography technician or nurse takes the patient to the image generating apparatus 2 (ultrasonic diagnosis apparatus 2a, endoscopic apparatus 2b, or CR apparatus 2c), carries out photography with the target body part of that patient as the photographic subject, and generates the image data of captured image. For example, when the image generating apparatus 2 is the CR apparatus 2c, photography is carried out using the radiographing apparatus 22, the cassette on which radiographing has been completed in the radiographing apparatus 22 is set in the reading apparatus 23, and the radiation image recorded in the cassette is read out. In the image generating apparatus 2, photography and generation of image data are carried out according to the operations by the person carrying out photography, and the above described UID is added to the generated image data and is transmitted to the control apparatus 3.

Upon oral interview, for example, if it has been decided that testing such as measurement of blood pressure, body temperature, electrocardiogram is necessary, a doctor or a nurse carries out the testing for the patient using the testing apparatus 4. In the testing apparatus 4, the above mentioned UID is added to the test data obtained by testing and is transmitted to the control apparatus 3.

When photography or testing is completed, the doctor, at the control apparatus 3, displays and refers to the photographed image received from the image generating apparatus 2 or the test result received from the testing apparatus 4, and carries out examination and diagnosis of the patient.

The above is the broad flow at the time of examining a patient. Correspondence of the patient data is established in the control apparatus 3 with the image data generated by the image generating apparatus 2 and with the test data obtained from the testing apparatus 4. Here, since the doctor displays the image data or the test result of the patient using the control apparatus 3 and carries out diagnosis of the patient, the control apparatus 3 is displaying, during the examination of the patient, the captured image or test results of a past date or obtained on that day related to the patient who is the target of examination.

The captured image or test result of a previous date or obtained on that day related to the patient who is the target of examination are displayed in the viewer screen for viewing these, for example, in the medical care summary screen 351.

Figure 4A:
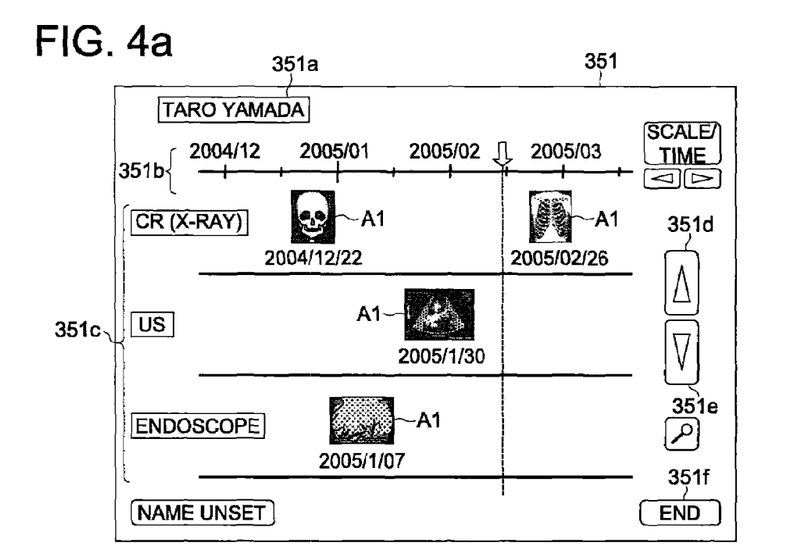
FIG. 4 is a diagram showing an example of medical care summary screen displayed in the display section of FIG. 3.
Figure 4B:
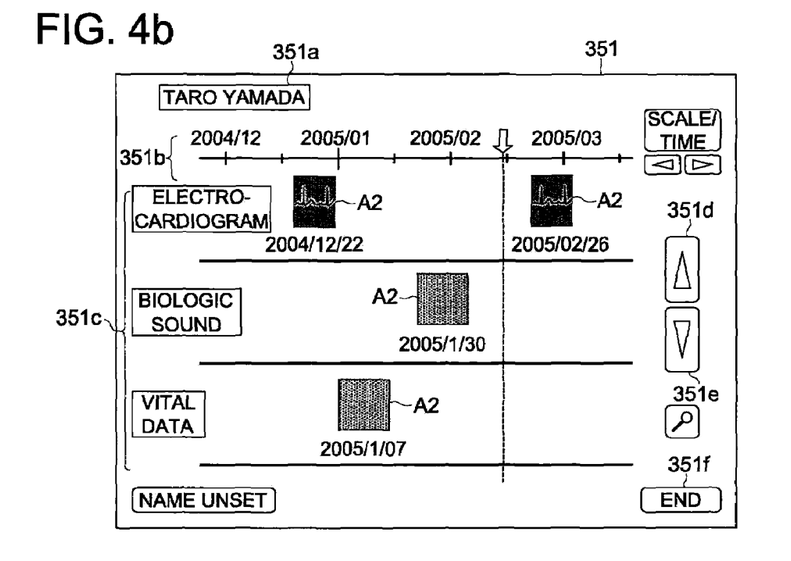

FIG. 4 shows an example of a medical care summary screen 351 of a patient who is the target of diagnosis. When the patient information of a patient of the examination target is input from the input section 34, a medical care summary screen 351 is the screen that is displayed showing a list in temporal sequence of the photography and tests conducted for that patient. A medical care summary screen 351 has patient information 351a, time axis 351b, medical care summary display area 351c, UP scroll button 351d, DOWN scroll button 351e, and END button 351f. In the medical care summary display area 351c, thumbnail images A1 of the images captured regarding the patient of the examination target are displayed classifying them for each image generating apparatus 2 in correspondence with the time axis 351b. Further, icons A2 (these icons are hereinafter referred to as test icons) indicating that test data has been obtained are displayed in the medical care summary area 351c at positions along the time axis 351b corresponding to the date and time at which test data was obtained, for each testing apparatus 4. The information in the screen shown in FIG. 4(b) is the information that is the continuation of the information in the screen shown in FIG. 4(a), and is displayed when the DOWN scroll button 351e is pressed for a prescribed number of times (for a prescribed duration) from the screen shown in FIG. 4(a). When a thumbnail image A1 is pressed using the input section 34, the captured image corresponding to the pressed thumbnail image A1 is displayed. By pressing a test icon A2 pressed using the input section 34, it is possible to regenerate the test data corresponding to the pressed test icon A2. By pressing the END button 351f, it is possible to close that medical care summary screen 351.

Here, the doctor, at the time of oral interview, inputs in the control apparatus 3, the patient information of the patient of the examination target and displays the medical care summary screen 351 and captured images of that patient, and based on the captured images or test data of the past and on the current state of the patient, determines the number of photographs or the direction of photographing and requests the photographing person to carry out photographing or performs testing. Therefore, as a rule, the patient of the examination target in the control apparatus 3 and the patient whose image data and test data have been received are the same. However, when an emergency patient comes, or in the case of a re-examination in which it is sufficient to carry out photography (or testing) with the same conditions as during the previous time, or when there are many patients who are waiting, photography is done in between interrupting the normal sequence. In this case, it is possible that the patient of the received image data or test data is not the same as the patient who is currently the target of examination. In addition, there are cases in which it is necessary to display images or test results and carry out examination of a patient who has been photographed interrupting the normal sequence such as an emergency patient instead of the patient whose medical care summary screen 351 is being displayed and who is currently the target of examination.

Figure 5:
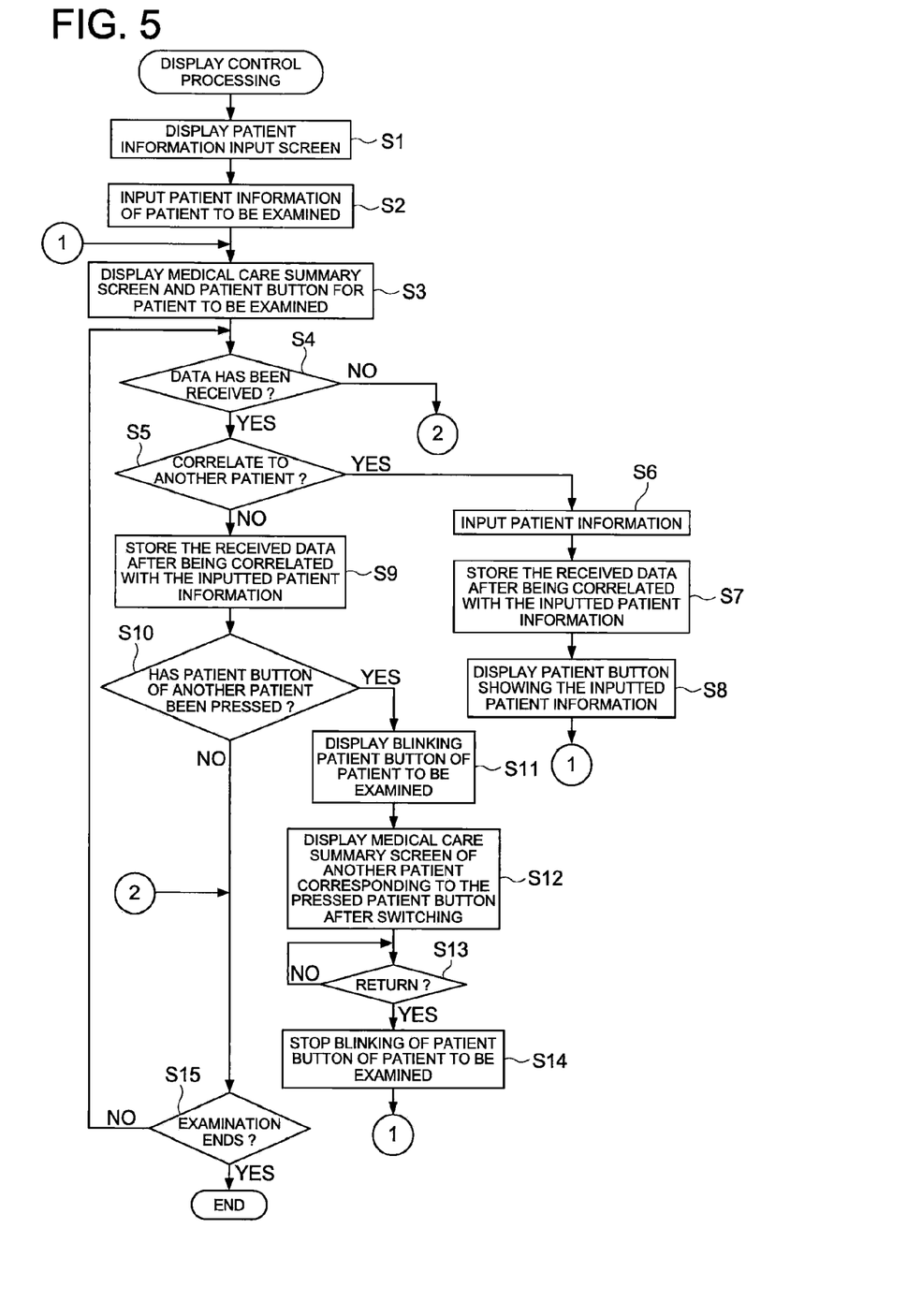
FIG. 5 is a flow chart showing the display control processing executed by the CPU of FIG. 3.

Here, while on the one hand, in the control apparatus 3, the display control processing shown in FIG. 5 is executed, and basically, the medical care summary screen 351 of the patient whose patient information has been input as the target patient of examination is displayed in the display section 35, and the image data or the test data received from the image generating apparatus 2 or from the testing apparatus 4 are stored after establishing correspondence with the patient information that has been input as the target of examination, on the other hand, it is made possible, upon receiving an instruction from the input section 34, to establish correspondence of the received image data or test data with the patient information of a different patient, and to change the screen display in the display section 35 from the medical care summary screen 351 of the patient who is the target of examination to the medical care summary screen 351 of a different patient.

In the following, the display control processing is described referring to FIG. 5. This is the processing that is realized by the software processing due to the coordinated operation of the CPU 31 and the display control processing programs stored in the storage section 33 at the time a prescribed operation is input instructing the display of a patient information input screen (not shown in the figure) for inputting the patient information of the patient who is to be the target of examination. The display control means is realized due to the execution of this processing.

To begin with, via the communication section 36, a patient information list transmission request is transmitted to the reception apparatus 5 and the data of the patient information list is obtained from the reception apparatus 5, and based on the received data, the patient information input screen is displayed in the display section 35 (Step S1). Here, in the patient information input screen, although not shown in the figure, a list of the patient information of the patients who were received on that day is being displayed, and it is possible to enter the patient information of the patient who is to be made the target of examination by the doctor selecting using the clicking of a mouse of the input section 34 at the patient information of the patient who is to be made the target of examination. In other words, a patient information input means is realized by the input section 34 and the patient information input screen. Further, in the patient information input screen, although it is also possible to have a configuration by which it is possible to input the patient information directly from the keyboard, but as has been described above, it is desirable to have a configuration in which the selection is made from the patient information list because errors in inputting can be prevented and time shortening can be achieved.

When the information of the patient who is to be made the target of examination is input using the input section 34 from the patient information input screen (Step S2), the medical care summary screen 351 of the patient who is the target of examination and the patient button B0 (see FIG. 6) displaying the patient information that has been input are displayed in the screen in the display section 35 (Step S3). In concrete terms, to begin with, not only the image data that has been stored in the image data base 38 with correspondence established with the patient information that has been input is extracted, but also the test data that has been stored in the test information data base 39 with correspondence established with the patient information that has been input is extracted, and a medical care summary screen 351 showing the thumbnail images A1 of the extracted images and the test icons A2 of the extracted test data is displayed in the display section 35. Next, a patient button B0 is generated displaying the patient information that has been input and is displayed in the screen in the display section 35.

After displaying the medical care summary screen 351 and the patient button B0, either image data is received from an image generating apparatus 2 by the communication section 36, or, test data is received from a testing apparatus 4 via the I/F 37. When the received data (the received image data or test data) is stored in the received data storage section 321 (YES in Step S4), in the display section 35, a pop up display of a correspondence establishment instruction screen 352 is made in the display section 35 for inputting the instruction of whether to establish correspondence of the received data with the patient who is the current target of examination or to establish correspondence with some other patient.

Figure 7:
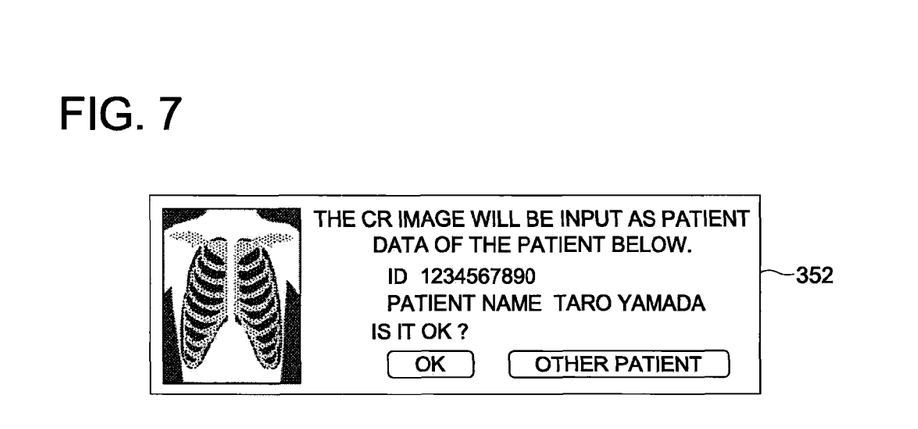
FIG. 7 is a diagram showing an example of the correspondence establishment instruction screen displayed in the display section of FIG. 3.

FIG. 7 shows an example of the correspondence establishment instruction screen 352. As is shown in FIG. 7, in the correspondence establishment instruction screen 352, the patient information of the patient who is currently being the target of examination, the thumbnail image (or the test icon) of the received data, a message confirming whether or not to establish correspondence of the received data with the patient who is currently the target of examination (the patient whose patient information is being displayed), an "OK" button for instructing to establish correspondence with the patient who is currently the target of examination, and a "Other Patient" button for instructing to establish correspondence with some other patient are being displayed.

When an instruction is input to establish correspondence of the received data with a patient other than the patient who is currently the target of examination by pressing the "Other Patient" button using the mouse of the input section 34 in the correspondence establishment instruction screen 352 (YES in Step S5), a patient information input screen is displayed in the display section 35 for inputting the patient information, and when the patient information is input from that screen (Step S6), if the received data is image data, that image data is stored in the image data base 38 while establishing correspondence with the patient information input in Step S6, or, if the input data is test data, that test data is stored in the test information data base 39 while establishing correspondence with the patient information input in Step S6 (Step S7). Further, a patient button Bn (n=1, 2, ... ) displaying the patient information of a patient whose patient information was input in Step S6, other than the patient who is the target of examination is generated and is displayed in the top part of the screen of the display section 35 (Step S8). Next, the operation returns to Step S3, and the medical care summary screen 351 of the patient who is the target of examination is displayed. The establishment of correspondence between the received data and the patient information is done, for example, by adding the patient information as associated information to the received data.

Regarding the patient information input screen in Step S6, similar to Step S1, a patient information list transmission request is transmitted to the reception apparatus 5 and the data of the patient information list is obtained from the reception apparatus 5, and based on the obtained data, the patient information input screen displaying the patient information list is displayed in the display section 35. By the doctor selecting by clicking with the mouse of the input section 34, the patient information in the patient information input screen, it is possible to input the patient information (the patient information of a different patient) with which correspondence is to be established for the received data. In the patient information input screen, it is also possible to have a configuration by which it is possible to input the patient information directly from the keyboard. Further, the patient information input screen in Step S6 is a screen for inputting the patient information of a different patient, and is not one for inputting the patient information of a patient who is to be the target of examination.

Figure 6:
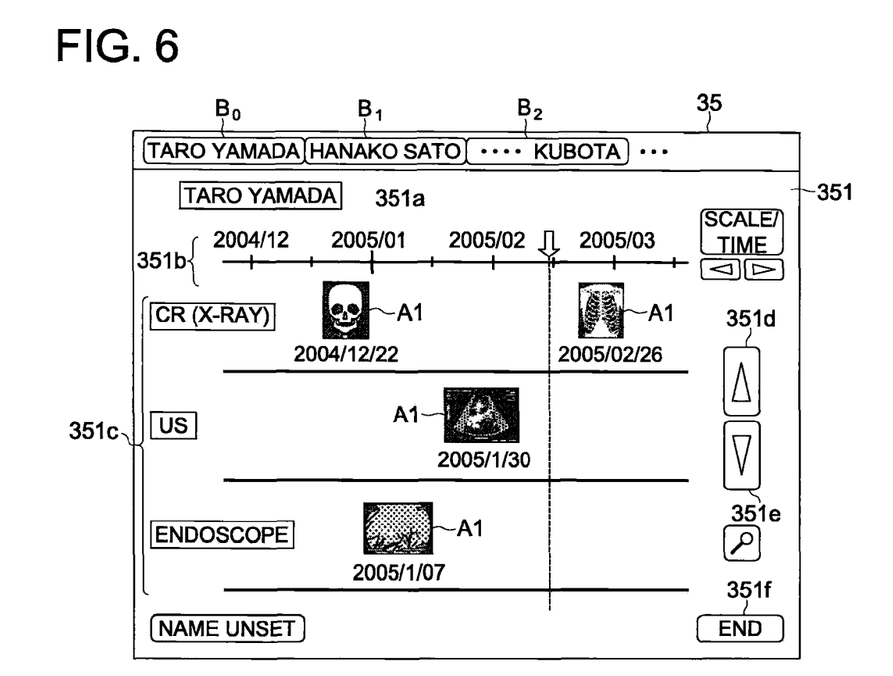
FIG. 6 is a diagram showing an example of a screen displayed in the display section of FIG. 3.

FIG. 6 shows an example of a screen of the display section 35 which is displayed in Step S3 after passing through Step S8. As is shown in FIG. 6, in the top part of the screen in the display section 35, the patient button B0 displaying the patient information that was input in Step S2 as the target of examination, the patient button Bn displaying the patient information of a different patient input in Step S8, and the medical care summary screen 351 of the patient who is the target of examination are being displayed. By the doctor pressing the patient button Bn using the mouse of the input section 34, an instruction can be input to change the screen display of the display section 35 to the medical care summary screen 351 of the patient whose patient information is being displayed in that pressed patient button Bn. In other words, the patient buttons Bn corresponds to patient selection buttons. Further, in Step S8, it is desirable that a judgment is made as to whether or not the patient information input in Step S6 is different from the patient information that is being displayed already in the patient button Bn, and if it is different, a new patient button Bn is preferably generated and displayed.

On the other hand, when the instruction is given to establish correspondence of the received data with the patient who is currently the target of examination (NO in Step S5) by pressing the "OK" button using the mouse of the input section 34 in the correspondence establishment instruction screen 352, if the received data is image data, that image data is stored in the image data base 38 while establishing its correspondence with the patient information input in Step S2, and if the received data is test data, that test data is stored in the test information data base 39 while establishing its correspondence with the patient information input in Step S2 (Step S9).

Next, a judgment is made as to whether or not the patient button Bn of a different patient was pressed using the input section 34. When it is judged that it was pressed (YES in Step S10), in addition to displaying in a blinking manner the patient button B0 of the patient who is currently the target patient of examination (Step S11), the screen display is changed to the medical care summary screen 351 of the patient corresponding to the patient button Bn which was pressed on the display section 35 (Step S12). In specific terms, to begin with, in addition to extracting the image data in the image data base 38 having correspondence established with the patient information corresponding to the patient button Bn, the test data stored in the test information data base 39 having correspondence established with the patient information corresponding to the patient button Bn is extracted, and in the display section 35, a medical care summary screen 351 is displayed displaying the thumbnail image A1 of the extracted image data and the test icon A2 of the extracted test data.

Further, although the medical care summary screen 351 of a different patient is roughly similar to the medical care summary screen 351 shown in FIG. 4 of a patient who is the target of examination, instead of the END button 351f, a "RETURN" button is displayed. This is the button for giving an instruction to end the interrupting display of the medical care summary screen 351 of another patient, and to return to the display of the medical care summary screen 351 of the original patient who is the target of examination.

When the "RETURN" button is pressed using the mouse of the input section 34 in the medical care summary screen 351 of another patient (YES in Step S13), the blinking of the patient button of the patient who is the target of examination which was being displayed in a blinking manner is stopped (Step S14), the processing returns to Step S3, and the medical care summary screen 351 of the patient who is the target of examination is displayed.

On the other hand, in Step S10, if it is judged that the patient button Bn of a different patient has not been pressed (NO in Step S10), the processing proceeds to Step S15, a judgment is made as to whether or not an instruction has been input to end the examination of the patient who is currently the target of examination by pressing the "END" button 351f using the mouse of the input section 34, and if it is judged that the examination end instruction has not been input (NO in Step S15), the processing returns to Step S4. This processing is ended if an instruction has been input to end the examination of the patient who is currently the target of examination by pressing the "END" button 351f using the mouse of the input section 34 (YES in Step S15).

Further, when the display control processing ends, the medical care summary screen 351 of the patient who is the target of examination is closed, and although even the patient button B0 of the patient who is the target of examination is erased from the display section 35, if the patient button Bn of another patient is being displayed at the time the examination ends, it can be made possible to set any one of the patients whose patient button Bn is being displayed as the patient who is the target of examination. For example, at the time an instruction to end of examination of a patient is made, in the display section 35, a pop up display of a screen displaying a message can be also made such as "Do you wish to set a target patient for examination?" and a list of the patient information which is displayed in the patient buttons Bn, to set the patient information that is selected by clicking the mouse of the input section 34 as the patient information of the next patient who is to be the target of examination, and to display the medical care summary screen 351 of the patient whose patient information has been selected.

As has been described above, according to a control apparatus 3 of a small-scale diagnostic system 1, when the patient information of a patient who is to be the target of examination is input using the input section 34, the medical care summary screen 351 is displayed for showing the captured images or others, of the patient whose patient information has been input. If either an image data is received from an image generating apparatus 2 via the communication section 36 or if test data is received from a testing apparatus 4 via the I/F 37, a pop up screen is displayed asking whether correspondence of the received data is to be established with the patient who is the current target of examination or with another patient. If an instruction is input from that screen to establish correspondence with another patient and the patient information of another patient is input, the received data is stored in the image data base 38 or the test information data base 39 while establishing correspondence with the patient information that has been input, and also, a patient button Bn is generated displaying the patient information of the other patient whose patient information has been input and is displayed in the display section 35. When the patient button Bn of another patient is pressed while the medical care summary screen 351 of a patient who is the current target of examination is being displayed, the screen display in the display section 35 is changed to the display of the medical care summary screen 351 of the patient whose patient button has been pressed.

Therefore, when the doctor is making the screen display of the captured images and test results of a patient who is the target of examination in the control apparatus 3, if the data of a different patient is received from an image generating apparatus 2 or a testing apparatus 4, and if the doctor wishes to view the captured image or test results of that other patient and to carry out examination and diagnosis, by using a simple operation of pressing the patient button it is possible to change the screen display to the image display or others, of that other patient, and it becomes possible for the doctor to carry out diagnosis by the image efficiently in a small-scale facility such as that of a medical practitioner's office.

Further, in the patient button, since the patient information of the destination of changing screen display due to pressing that patient button is being displayed, the doctor can recognize the screen display of which patient the doctor is switching to.

Further, since a patient button is generated every time a correspondence is established of an image data received from an image generating apparatus with some patient information that is different from the patient information that has already been displayed in the patient buttons, it is possible to display in the display section only the patient buttons of the patients who have been photographed and who need diagnosis, and hence the degree of convenience increases.

Further, since the configuration is such that, after carrying out screen display of patients other than the patient who is the target of examination, it is not possible to carry out the screen display of a patient other than the patient who is the target of examination unless the screen display is first returned to the screen display of the patient who is the target of examination by pressing the "RETURN" key, the problem can be prevented that the doctor cannot recognize the image of which patient is being displayed because of repeatedly changing the patient selection and hence carrying out diagnosis wrongly while believing that the captured image being displayed is of some other patient can be prevented.

Further, during the screen display of a patient other than the patient who is the target of examination, since the patient button displaying the patient information of the patient who is the target of examination is being displayed in a blinking manner, the doctor can recognize that the screen display has been switched to that of a patient other than the patient who is the target of examination.

Further, the content described in the above preferred embodiment is merely one preferred example of a small-scale diagnostic system 1 according to the present invention, the present invention shall not be construed to be limited to this.

For example, in the above preferred embodiment, although the descriptions were made taking an image generating apparatus 2 to be an ultrasonic diagnostic apparatus, an endoscopic apparatus, and a CR apparatus, it is not necessary to limit to these, and this can be, for example, a CT apparatus, or a digital camera that photographs the external view of the body such as skin, etc.

As has been described above, according to the present invention, when the image data of a different patient is received from an image generating apparatus while a doctor is making screen display of the image data of one patient in a medical image management apparatus, if the doctor wishes to display in the screen the received image data of the other patient and to carry out examination and diagnosis, it is possible to change the screen display to the image data of the other patient by making a simple operation of pressing the patient selection button, and in a small-scale facility such as that of a medical practitioner's office, it is possible to provide a small-scale diagnostic system and display control method with which a doctor can carry out image diagnosis efficiently.

Further, regarding the detailed configurations and detailed operations of constituent elements of a small-scale diagnostic system or a display control method according to the present invention, it is possible to make suitable modifications within a range that does not deviate from the scope or intent of the present invention.

The invention claimed is:
1. A small-scale diagnostic system comprising:
an image generating apparatus which photographs a patient body part which is a target of diagnosis and which generates and transmits image data; and
a medical image management apparatus which is connected with the image generating apparatus and which receives the image data generated in the image generating apparatus and stores the received image data and patient information of a plurality of patients in a storage section while establishing correspondence between the received image data and the patient information,
wherein the medical image management apparatus comprises:
a display section which conducts screen display of the image data stored in the storage section for each patient after the correspondence between the image data and the patient information has been established; and
a display control section which displays in the display section while screen display of image data of one patient is conducted, a patient selection button for inputting an instruction for changing the screen display to screen display of image data of another patient, and which changes the screen display of image data in the display section to the screen display of another patient in accordance with instruction input operation of the displayed patient selection button,
wherein the patient selection button allows to select a patient for the screen display other than the patient whose screen display currently being conducted, and displays a patient name of the patient to be selected,
wherein whenever the correspondence is established between patient information of a new patient other than a patient whose name is being displayed already in the patient selection button and new image data received from the image generating apparatus, the display control section generates and displays a new patient selection button displaying a patient name of the new patient in the display section.

2. A display control method of image data in a medical image management apparatus, the method comprising the steps of:
receiving image data generated in an image generating apparatus which photographs a patient body part which is a target of diagnosis and generates and transmits the image data;
storing the received image data and patient information of a plurality of patients in a storage section while establishing correspondence between the received image data and the patient information;
conducting screen display of the image data stored in the storage section for each patient in a display section after the correspondence between the image data and the patient information has been established;
displaying in the display section while screen display of image data of one patient is conducted, a patient selection button for inputting an instruction for changing the screen display to screen display of image data of another patient,
wherein the patient selection button allows to select a patient for the screen display other than the patient whose screen display currently being conducted, and displays a patient name of the patient to be selected,
changing the screen display of image data in the display section to the screen display of another patient in accordance with instruction input operation of the displayed patient selection button; and
generating and displaying a new patient selection button displaying a patient name of a new patient in the display section, whenever the correspondence is established between patient information of the new patient other than a patient whose name is being displayed already in the patient selection button and new image data received from the image generating apparatus.

* * * * *